United States Patent [19]

Voges et al.

[11] Patent Number: 4,644,086

[45] Date of Patent: Feb. 17, 1987

[54] PROCESS AND CATALYST FOR THE ORTHOMETHYLATION OF PHENOLS

[75] Inventors: Heinz-Werner Voges, Dorsten; Arno Siegmar Schmidt, Münster, both of Fed. Rep. of Germany

[73] Assignee: Huels Aktiengesellschaft, Marl, Fed. Rep. of Germany

[21] Appl. No.: 767,014

[22] Filed: Aug. 19, 1985

[30] Foreign Application Priority Data

Aug. 17, 1984 [DE] Fed. Rep. of Germany ....... 3430222

[51] Int. Cl.$^4$ ............................................. C07C 37/16
[52] U.S. Cl. ................................................... 568/804
[58] Field of Search .................... 568/804, 794, 789

[56] References Cited

U.S. PATENT DOCUMENTS

| | | | |
|---|---|---|---|
| 3,751,488 | 8/1973 | van Sorge | 568/804 |
| 3,764,630 | 10/1973 | van Sorge | 568/804 |
| 4,227,024 | 10/1980 | Leach | 568/804 |
| 4,471,149 | 9/1984 | Adey et al. | 568/804 |

FOREIGN PATENT DOCUMENTS

| | | | |
|---|---|---|---|
| 2127083 | 12/1971 | Fed. Rep. of Germany | 568/804 |
| 37942 | 9/1972 | Japan | 568/804 |
| 49236 | 5/1973 | Japan | 568/804 |
| 101330 | 8/1975 | Japan | 568/804 |
| 0208244 | 12/1984 | Japan | 568/804 |
| 7512390 | 4/1976 | Netherlands | 568/804 |

*Primary Examiner*—Werren B. Lone
*Attorney, Agent, or Firm*—Millen & White

[57] ABSTRACT

A process and catalyst for the orthomethylation of phenols having at least one free ortho position, wherein the phenols are reacted with methanol in a molar ratio of about 1:1 to 1:10 at about 250°–340° C. in the gaseous phase under a pressure of about 1–4 bar absolute and with rates per unit volume (LHSV) of about 0.05–3 $h^{-1}$ in the presence of an iron oxide catalyst. This catalyst consists essentially of (a) iron oxide, (b) molybdenum oxide or tungsten oxide (c) one or several oxides of the elements magnesium, calcium, barium, lanthanum, cerium or manganese in a metal-atomic ratio of about (a):(b):(c): of 100:0.2–10:0.2–10.

22 Claims, No Drawings

PROCESS AND CATALYST FOR THE ORTHOMETHYLATION OF PHENOLS

BACKGROUND OF THE INVENTION

The use of pure iron oxide, $Fe_2O_3$, as a catalyst in the orthomethylation of phenol has been disclosed in British Pat. No. 717,588. This catalyst exhibits a high alkylating activity even at a relatively low temperature, but its moderate selectivity for ortho-alkylation as well as relatively short operating life make the catalyst economically unattractive.

Attempts have been made to improve the properties of pure iron oxide catalysts by means of additional oxide components. Numerous catalyst compositions have become known containing, besides the primary iron oxide component, chromium oxide in particular. DOS No. 2,428,056 (British Pat. No. 1,428,057) describes catalysts having the composition $Fe_2O_3/Cr_2O_3/(SiO_2)/K_2O$, exemplifying a metalatomic ratio of $100:1:(10^{-4})$ $2^x10^{-3}$. A binary iron oxide/ chromium catalyst is described in Published Japanese Pat. No. 76012-610 and a catalyst containing iron oxide, chromium oxide, indium oxide, silicon oxide and potassium oxide is claimed in Japanese Pat. No. 58 109 436. Furthermore, catalysts consisting predominantly of iron oxide are known having the compositions Fe/Cr/Ge (or Ga, Nb) (European Patent Publication No. 0 019 476), Fe/Cr/Ge (or Si)/Mn (or La) [German Pat. No. 3,103,839 (U.S. Pat. No. 4,227,024 and British Pat. No. 2,072,674)] as well as Fe/Cr/Sn/K (U.S. Pat. No. 4,227,024), Fe/Cr/Zr (or Cd and others)/$K_2CO_3$ (European Patent Publication No. 0 050 937), Fe/Cr/Ce (European Patent Publication No. 0 081 647). Thus, all of the prior art iron oxide combinations contain, as an essential component, the oxide of trivalent chromium.

In contrast thereto, industrially useful iron oxide catalysts containing, in place of the oxide of trivalent chromium, the oxides of hexavalent molybdednum or hexavalent tungsten have not been disclosed to be useful for phenol methylation. Although the above-cited U.S. Pat. No. 4,227,024 mentions a binary mixture consisting of iron oxide and molybdenum oxide ($MoO_3$), this oxide mixture is said in the patent to be useless for phenol methylation. Also, by direct comparison of the binary oxide mixtures Fe/Cr, Fe/Mo, Fe/W under otherwise identical experimental conditions, it is found that at high total selectivity toward ortho-alkylation, a drop in selectivity toward 2,6-dimethylphenol occurs if there is a substitution of Fe oxide/Cr oxide by Fe oxide/Mo oxide and especially if there is substitution by Fe oxide/W oxide.

SUMMARY OF THE INVENTION

An object of the invention is to provide a novel improved gaseous phase catalytic process for the orthomethylation of phenol compounds having at least one hydrogen atom in the ortho position.

Another object is to provide a process having one or more, and preferably all of the following attributes: high activity, high selectivity, and long operating lifetime of the catalyst.

An additional object is to provide a catalytic system for the process.

Upon further study of the specification and appended claims, further objects and advantages of this invention will become apparent to those skilled in the art.

Suprisingly, and contra to the teaching in U.S. Pat. No. 4,227,024, applicants have developed an industrially feasible process for the selective orthomethylation of phenols having a hydrogen atom in at least one ortho position, comprising reacting these phenols with methanol in the gaseous phase, at preferably about 270°-340° C. in the presence of a catalyst comprising iron oxide, and, according to this invention, also containing a combination of the oxides of molybdenum and/or tungsten with oxides of the alkaline earth metals magnesium, calcium, barium, with oxides of the rare earth metals lanthanum and cerium, or manganese.

These oxide mixture catalysts exhibit high activity and selectivity for ortho-alkylation over prolonged time periods.

It is possible according to the process of the invention to produce in high yields, for example, orthocresol from phenol, 2,6-dimethylphenol from phenol and/or orthocresol 2,3,6-trimethylphenol from metacresol, and 2,3,5,6-tetramethylphenol from 3,5-dimethylphenol.

Catalysts useable in the process of this invention are obtained by combining (a) iron oxide, with (b) molybdenum oxide and/or tungsten oxide in conjunction with (c) one or more of the oxides of the alkaline earth metals, specifically magnesium, calcium or barium, or of the rare earths specifically lanthanum or cerium, or of manganese. The major part of the catalyst, i.e. between about 80 and about 99% w/w, consists of iron oxide, suitably $Fe_2O_3$ or $Fe_3O_4$. In use $Fe_2O_3$ may be converted to $Fe_3O_4$. Aside from the iron oxide the catalyst comprises up to 20% w/w, preferably up to 8% and most preferably not more than 1-2% of the other oxides. As an example a typical catalyst according to this invention consists of $Fe_2O_3$ 98.3% w/w, $WO_3$ 1.45% w/w, and MgO 0.25% w/w. This composition corresponds to a metalatomic ratio of Fe:W:Mg of about 100:0.5:0.5. The molybdenum or tungsten component may be used alone or in admixture.

Combinations of the various alkaline earths, combinations of the various rare earths, combinations of the alkaline earths with the rare earths all optionally in combination with and/or manganese are also contemplated in the invention.

The preferred oxide mixtures of this invention typically exhibit metal-atomic ratios of Fe/Mo or W/alkaline earth metal or rare earth metal or manganese, i.e., (a):(b): (c), respectively, of about 100:0.2–10:0.2–10, more preferably of about 100:0.4–4:0.4–4. The preferred metalatomic ratio of Fe/W/Ba or Mg is 100:0.2–2:0.2–2.

Prefered oxide mixtures are those comprising iron oxide, tungsten oxide and one or more oxides of magnesium, calcium, barium, lanthanum, cerium or manganese. Still more preferable oxide mixtures are those comprising iron oxide, tungsten oxide and one or several oxides of barium, cerium or manganese.

Preferred specific ternary systems include but are not limited to Fe/Mo/Ca, Fe/Mo/Ba, Fe/Mo/Ce, Fe/Mo/Mn, Fe/W/Mg, Fe/W/La, Fe/W/Ba or Fe/W/Ce.

Preferred systems having more than three oxides include but are not limited to Fe/W/Ba/Mn, Fe/Mo/Ce/Mn, Fe/W/Mg/Mn. Manganese oxide as a fourth component appears to have the effect of imparting structural stability to the catalyst) resulting in a longer service life. Therefore its addition will he a preferred embodiment of the invention.

The catalysts of this invention are prepared according to conventional methods, for example by intimate mixing of the oxide components having a particle size range of preferably about 1 to 10 μm (micrometers) or preferably by coprecipitation of the hydroxides and oxides, respectively, from aqueous solutions of the metallic salts. Coprecipitation can be accomplished with, for example, molybdenum in the form of ammonium molybdate, or tungsten in the form of ammonium tungstate, coprecipitated with bases, such as aqueous ammonia solution, alkaline solutions or alkali carbonate solutions. The iron hydroxide, for example iron (III) hydroxide precipitate, containing the oxides and/or hydroxides of the additive components in uniform distribution, is washed with water to remove foreign ions and excess base that may be present, dried at about 130° C., and ground into a powder. The pulverulent oxide mixture, to which may optionally be added up to 10% by weight of an inert additive, such as graphite, can be pressed or shaped into molded elements of a suitable size, for example into tablets or extruded shapes. After calcining at temperatures of about 400°–500° C., the molded catalyst articles are ready for the gaseous phase reaction of the phenols with methanol. In a preferred embodiment, the molded elements are filled into reaction tubes having internal diameters of up to 50 mm, preferably up to 32 mm, said tubes being immersible in a thermostatically controlled heating bath. The reactants (phenolic compound and methanol) are vaporized in a specific molar ratio prior to entering the catalyst-filled reaction tube; suitably by feeding a solution of the phenolic compound in the stoichiometric amount of methanol to a vaporizer/preheater and conducting the vapor mixture exiting therefrom over the catalyst.

The reaction preferably takes place under the following conditions wherein the molar ratio of phenolic compound to methanol is from about 1:1 to 1:10, the flow rate per unit volume (LHSV) is about 0.05–3h$^{-1}$, calculated for the mixture of reactants prior to vaporization, the reaction temperature is about 270°–400° C., and more preferably is about 300°–350° C.; and the reaction pressure is about 1–4 bar absolute.

Under these reaction conditions, it is possible to effect practically complete conversion of the phenolic compound employed, the desired ortho-alkylation products being formed with high selectivity.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Comparative Examples A, B, and C

Binary catalysts Fe/Cr, Fe/Mo and Fe/W are prepared by coprecipitation of the hydroxides/oxides with 10% aqueous $NH_3$ solution from aqueous solutions of respectively 404 g of $Fe(NO_3)_3.9H_2O$ with Comparative Example A: 2 g of $Cr(NO_3)_3.9H_2O$
Comparative Example B: 0.87 g of $(NH_4)_6Mo_7O_{24}.4H_2O$
Comparative Example C: 1.3 g of $(NH_4)_{10}W_{12}O_{41}.7H_2O$ The catalysts, prepared as described above, are filled into reaction tubes (internal diameter 22 mm) and temperature-controlled in a thermostated bath. Phenol/methanol vapors (molar ratio 1:5) are conducted over the catalysts under normal pressure. LHSV in all three instances is 0.09 h$^{-1}$, the reaction temperature is 323° C. The product vapors discharged from the reaction tubes are condensed in water-cooled coolers; the thus-liquefied product mixtures are analyzed by gas chromatography. With the binary catalysts, the following results are obtained after an operating period of 76 hours:

| Comparative Example | Oxide Components Metal-Atomic Ratio | Phenol Conversion (%) | Selectivity (%) with Respect to | | |
|---|---|---|---|---|---|
| | | | o-Cresol | 2,6-DMP* | Ortho-methylation | Tri-methylphenols |
| A | Fe/Cr 100/0.5 | 99.9 | 5.0 | 92.7 | 97.7 | 2.3 |
| B | Fe/Mo 100/0.5 | 99.9 | 11.9 | 84.9 | 96.8 | 3.2 |
| C | Fe/W 100/0.5 | 99.6 | 21.4 | 75.0 | 96.4 | 3.6 |

*2,6-DMP = 2,6-Dimethylphenol

The comparative examples demonstrate that the binary Fe/Mo catalyst shows weaker activity for the desired secondary alkylation (2,6-dimethylphenol formation) than the binary Fe/Cr catalyst, and that the binary Fe/W catalyst exhibits a weaker secondary alkylating activity than the Fe/Mo catalyst.

EXAMPLES 1–4

The following examples represent ternary catalysts according to this invention, based on Fe/Mo and containing additionally a further oxide component. They are prepared by the coprecipitating method from respectively 404 g of $Fe(NO_3)_3.9H_2O$ and 087 g of $(NH_4)_6Mo_7O_{24}.4H_2O$, as well as Example 1: 1.18 g of $Ca(NO_3)_2.4H_2O$
Example 2: 1.24 g of $Ba(NO_3)_2$
Example 3: 1.45 g of $Ce(NO_3)_3.6H_2O$
Example 4: 1.44 g of $Mn(NO_3)_2.6H_2O$ The precipitates, obtained by precipitating with aqueous ammonia from an aqueous solution, are press-molded into 3×3 mm tablets after filtration, washing and drying. These tablets are subsequently calcined at 450° C. in an air stream. Phenol/methanol vapor mixtures (molar ratio 1:5) are passed under 1 bar over the catalysts located in reaction tubes having an internal diameter of 22 mm. The rate per unit volume of the phenol/methanol feed mixture prior to vaporization is uniformly 0.08 h$^{-1}$. The following results are obtained after a testing period of 100 hours:

| Example | Catalyst Atomic Ratio | Reaction Temp. (°C.) | Phenol Conversion (%) | Selectivity (%) with Respect to | | Orthomethylation | Trimethylphenols |
|---|---|---|---|---|---|---|---|
| | | | | o-Cresol | 2,6 DMP* | | |
| 1 | Fe/Mo/Ca 100/0.5/0.5 | 324 | 99.7 | 11.7 | 82.4 | 94.1 | 4.2 |
| 2 | Fe/Mo/Ba 100/0.5/0.48 | 324 | 99.4 | 16.4 | 80.4 | 96.8 | 2.1 |
| 3 | Fe/Mo/Ce 100/0.5/0.33 | 320 | 99.3 | 12.2 | 85.4 | 97.6 | 2.0 |
| 4 | Fe/Mo/Mn 100/0.5/0.5 | 324 | 99.4 | 15.5 | 82.7 | 98.2 | 1.3 |

*2,6-DMP = 2,6-Dimethylphenol
Paracresol is formed with selectivities of <0.1%

EXAMPLE 5

The catalyst of Example 3 (Fe/Mo/Ce) is subjected to a long-term test over more than 1,000 hours. In this test, the reaction temperature at 1 bar is raised stepwise to the extent that the phenol conversion remains larger than 99%.

| Operating Time (h) | 70 | 380 | 730 | 1,150 |
|---|---|---|---|---|
| Reaction Temp. (°C.) | 319 | 322 | 324 | 326 |
| Phenol Conversion (%) | 99.6 | 99.7 | 99.5 | 99.6 |
| Selectivity Toward | | | | |
| Orthomethylation (%) | 97.4 | 97.9 | 98.2 | 98.5 |
| of This Toward | | | | |
| Orthocresol (%) | 10.0 | 10.2 | 10.3 | 10.5 |
| 2,6-DMP (%) | 87.4 | 87.7 | 87.9 | 88.0 |
| Trimethylphenols (%) | 2.2 | 2.0 | 1.2 | 1.1 |

Over the entire operating period, paracresol is formed only in selectivities of <0.1%. After the testing period of more than 1,000 hours, the catalyst is still fully active with high selectivity for orthomethylation products.

EXAMPLES 6–9

Ternary catalysts according to this invention based on Fe/W are prepared by the coprecipitation method from respectively 404 g of $Fe(NO_3)_3.9H_2O$, 1.32 g of $(NH_4)_{10}W_{12}O_{41}.7H_2O$, as well as
Example 6: 1.28 g of $Mg(NO_3)_2.6H_2O$
Example 7: 2.17 g of $La(NO_3)_3.6H_2O$
Example 8: 1.30 g of $Ba(NO_3)_2$
Example 9: 2.17 g of $Ce(NO_3)_3.6H_2O$ Under the same conditions as in Examples 1–4, phenol/methanol vapors (molar ratio 1:5) are conducted over the catalysts (tablets 3×3 mm) calcined at 450° C. After a testing period of 100 hours, the following results are obtained:

| Example | Catalyst Atomic Ratio | Reaction Temp. (°C.) | Phenol Conversion (%) | Selectivity (%) With Respect to | | Trimethylphenols | Methanol Loss* (%) |
|---|---|---|---|---|---|---|---|
| | | | | o-Cresol | 2,6-DMP | | |
| 6 | Fe/W/Mg 100/0.5/0.5 | 326 | 99.7 | 7.3 | 85.1 | 6.6 | 34 |
| 7 | Fe/W/La 100/0.5/0.5 | 320 | 99.6 | 8.0 | 89.3 | 1.9 | 39 |
| 8 | Fe/W/Ba 100/0.5/0.5 | 318 | 99.9 | 5.4 | 93.1 | 1.1 | 32 |
| 9 | Fe/W/Ce 100/0.5/0.5 | 320 | 99.1 | 7.2 | 90.0 | 2.0 | 40 |

*Methanol loss in the form of gaseous decomposition products ($H_2$, CO, $CO_2$) in % of feed
Paracresol is contained in the reaction products merely in traces below 0.1% by weight

EXAMPLE 10

A catalyst consisting of iron oxide, tungsten oxide and barium oxide in metal-atomic ratios of 100:2:0.6, prepared according to the coprecipitation method, is subjected to a test of over 2,000 hours under conditions as set forth in Example 5.
The following results are obtained:

| Operating Time (h) | 20 | 170 | 242 | 506 | 1,203 | 2,076 |
|---|---|---|---|---|---|---|
| Reaction Temp. (°C.) | 314 | 319 | 322 | 324 | 324 | 328 |
| Phenol Conversion (%) | 99.6 | 99.8 | 99.8 | 99.7 | 99.0 | 99.7 |
| Selectivity for Orthoalkylation (%) | 97.8 | 98.3 | 98.4 | 98.4 | 98.7 | 98.2 |
| Broken down to | | | | | | |
| o-Cresol (%) | 11.7 | 6.7 | 7.4 | 12.7 | 9.9 | 11.1 |
| 2,6-DMP (%) | 86.1 | 91.6 | 91.0 | 85.7 | 88.8 | 87.1 |
| Trimethylphenols (%) | 1.3 | 1.0 | 0.95 | 0.87 | 0.90 | 1.1 |
| Methanol Loss (%) | 28 | 32 | 33 | 34 | 34 | 35 |

The rate per unit volume (LHSV) during the entire operating period is 0.08 $h^{-1}$. At the end of the testing time, the catalyst is still fully active and exhibits high selectivity. Paracresol is formed only in traces of below 0.1% by weight. The methanol losses are relatively low.

EXAMPLE 11

A catalyst is produced by the coprecipitation method from 404 g of $FE(NO_3)_3.9H_2O$, 2.64 g of $(NH_4)_{10}W_{12}O_{41}.7H_2O$, 1.30 g of $Ba(NO_3)_2$ and 1.44 g of $Mn(NO_3)_2.6H_2O$. Aqueous ammonia solution is utilized for precipitating the hydroxide/oxide precipitate from the aqueous solution. The metal-atomic ratio of Fe-/W-/Ba/Mn is 100:1:0.5:0.5. The mixture, washed with water after filtration, then dried at 130° C., and pressed into tablets (3×3 mm), is calcined at 430° C. Phenol/-methanol vapors (molar ratio 1:5) are conducted at LHSV=0.1 h$^{-1}$ at 1 bar over the catalyst, which latter is located in a reaction tube with an internal diameter of 22 mm. After an operating period of 100 hours, phenol conversion, as per analysis by gas chromatography of the reaction product, is 99.4%; the internal reactor temperature at this point in time is maintained at 325.5° C. The selectivities for orthocresol, 2,6-dimethylphenol and trimethylphenols, respectively, are 8.2%, 90.1%, and 1.3%.

EXAMPLE 12

Using 10% aqueous sodium hydroxide solution, the metal hydroxides/oxides are precipitated from an aqueous solution of 404 g of Fe(NO$_3$)$_3$.9H$_2$O, 2.61 g of (NH$_4$)$_6$Mo$_7$O$_{24}$.4H$_2$O, 1.45 g of Ce(NO$_3$)$_3$.6H$_2$0 and 5.76 g of Mn(NO$_3$)$_2$.6H$_2$O (metal-atomic ratio Fe/Mo/-Ce/Mn=100:1.5:0.5:2.0. The precipitate is filtered off and washed with water, then dried, pulverized, pressed into 3×3 mm tablets, and the latter calcined at 420° C. Phenol/methanol vapors (molar ratio 1:5) are conducted at a rate per unit volume LHSV of 0.09 h$^{-1}$ over the catalyst, which latter is arranged in a reaction tube having an inner diameter of 22 mm (pressure 1 bar). After an operating period of 130 hours and at an internal reactor temperature of 322° C., the phenol conversion amounts to 99.4%, and the selectivity for orthocresol is 13.1%, for 2,6-dimethylphenol 84.2% and for trimethylphenols 1.8%. The reaction product contains only traces of paracresol amounting to <0.1% by weight.

EXAMPLES 13-15

Ternary catalysts according to this invention based on Fe/W/Mg are prepared by the coprecipitation method from respectively 250 g of Fe(NO$_3$)$_3$.9H$_2$O, 0.80 g of Mg(NO$_3$)$_2$.6 H$_2$O as well as
Example 13: 0.81 g of 5 (NH$_4$)$_2$O.12WO$_3$.7H$_2$O
Example 14: 0.66 g of 5 (NH$_4$)$_2$O.12WO$_3$.7H$_2$O
Example 15: 0.99 g of 5 (NH$_4$)$_2$O.12WO$_3$.7H$_2$O The precipitation and drying are performed under the same conditions as in Examples 1-4, the calcination is carried out at 400° C.

The Examples 13-15 are performed under conditions given in the table below and with a molar phenol/methanol ratio of 1/5.

EXAMPLES 16 and 17

The catalysts are prepared under the same conditions as in Examples 13-15. The experiments are performed with the same phenol/methanol ratio and furtheron under conditions given in the table below.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions. As an example paramethylation of phenols whose ortho-positions both are substituted can be achieved easily by using the catalysts of the invention.

What is claimed is:

1. In a process for the orthomethylation of a phenol having at least one free ortho position, said process comprising the step of reacting said phenol with methanol in the gaseous phase in the presence of a catalyst, the improvement which comprises conducting the reaction in contact with a catalyst consisting essentially of a combination of
    (a) iron oxide,
    (b) molybdenum oxide and/or tungsten oxide and
    (c) at least one oxide of magnesium, calcium, barium, lanthanum, cerium, or manganese
said oxide being in a metal-atomic ratio of
    (a):(b):(c) of 100:0.2–10:0.2–10.

2. A process according to claim 1, wherein the catalyst is used in a metal-atomic ratio of (a):(b):(c) of about 100:0.4–4:0.4–4.

3. A process according to claim 1, wherein the catalyst consists essentially of a combination of (a) iron oxide (b) tungsten oxide and (c) at least one oxide of magnesium, calcium, barium, lanthanum, cerium and/or manganese.

4. A process according to claim 3, wherein the catalyst consists of a combination of (a) iron oxide, (b) tungsten oxide, and (c) barium oxide.

5. A process according to claim 3, wherein the catalyst consists of a combination of (a) iron oxide, (b) tungsten oxide and (c) magnesium oxide.

6. A process according to claim 4 wherein the catalyst components are used in a metal-atomic ratio of (a):(b):(c) of about 100:0.2–2:0.2–2.

7. A process according to claim 1, wherein the molar ratio of the phenol to methanol is about 1:1 to 1:10.

8. A process according to claim 4, wherein the reaction temperature is about 270°–400° C.

9. A process according to claim 5, wherein the reaction pressure is about 1–4 bar.

10. A process according to claim 6, wherein the LHSV is about 0.05–3h$^{-1}$.

11. A process according to claim 1, wherein the starting material phenol is unsubstituted, or is orthocresol or metacresol.

12. A process according to claim 1, wherein the orthomethylated phenol is orthocresol, 2,6-dimethylphenol, 2,3,6-trimethylphenol or 2,3,5,6-tetramethylphenol.

| Example | metal-atomic ratio Fe/W/Mg | operating time (h) | LHSV (h$^{-1}$) | Reaction Temp. (°C.) | Reaction Pressure (bar) | Phenol Conversion (%) | Selectivity (%) with Respect to o-Cresol | 2.6-DMP | Trimethyl-phenols | Methanol Loss (%) |
| --- | --- | --- | --- | --- | --- | --- | --- | --- | --- | --- |
| 13 | 100/0.5/0.5 | 150 | 0.1 | 323 | 1 | 99.8 | 6.9 | 87.7 | 4.3 | 35 |
| 14 | 100/0.4/0.5 | 100 | 0.1 | 323 | 1 | 99.9 | 9.7 | 83.0 | 6.3 | 28 |
| 15 | 100/0.6/0.5 | 70 | 0.09 | 323 | 1 | 99.9 | 8.8 | 81.4 | 4.5 | 32 |
| 16 | 100/0.5/0.5 | 100 | 0.09 | 323 | 2 | 99.8 | 7.1 | 84.3 | 5.1 | 28 |
| 17 | 100/0.5/0.5 | 80 | 0.09 | 323 | 4 | 99.8 | 7.3 | 83.9 | 5.5 | 27.5 |

13. A process according to claim 1, wherein the catalyst is produced by coprecipitation of the oxides or hydroxides from an aqueous solution of the metallic salts with a base.

14. A process according to claim 10, wherein the catalyst is produced by coprecipitation of ammonium molybdate or ammonium tungstate with aqueous ammonia or an aqueous alkali carbonate solution.

15. A process according to claim 13, wherein the coprecipitate is washed with water until unbound ions and excess base are removed, dried at elevated temperature and pulverized.

16. A process according to claim 12, wherein the pulverized catalyst is molded into tablets and calcined at about 400°–500° C.

17. A process according to claim 16, wherein about 10% by weight of an inert material is added to the pulverized catalyst before molding.

18. A process according to claim 1, wherein component (b) of the catalyst consists essentially of tungsten oxide.

19. A process according to claim 15, wherein the catalyst system consists essentially of oxides of Fe/W/Mg, Fe/W/La, Fe/W/Ba, Fe/W/Ce, Fe/W/Ce, Fe/W/Ba/Mn or Fe/W/Mg/Mn.

20. A process according to claim 1, wherein the catalyst system consists of oxides of Fe/W/Mg, Fe/W/LA, Fe/W/Ba, Fe/W/Ce, Fe/W/BA/Mn or Fe/W/Mg/Mn.

21. A process according to claim 1, wherein the catalyst system consists of oxides of Fe/W/Mg.

22. A process according to claim 1, wherein said catalyst is free of silicon and alkali metals.

* * * * *

UNITED STATES PATENT AND TRADEMARK OFFICE
CERTIFICATE OF CORRECTION

PATENT NO. : 4,644,086

DATED : 2-17-87

INVENTOR(S) : Dr. Heinz-Werner Voges et al

It is certified that error appears in the above-identified patent and that said Letters Patent is hereby corrected as shown below:

Column 8, Line 55: (Claim 12)

reads: "phenol, 2,3,6,-trimethylphenol or 2,3,5,6-tetramethyl"

should read: --phenol, 2,3,6-trimethylphenol or 2,3,5,6-tetramethylphenol

Column 9, Claim 16, Line 17:

reads: "16. A process according to claim 12, wherein the"

should read: --16. A process according to claim 15, wherein the--

Signed and Sealed this

Twenty-fifth Day of August, 1987

*Attest:*

DONALD J. QUIGG

*Attesting Officer*      *Commissioner of Patents and Trademarks*